United States Patent [19]
Moldt et al.

[11] Patent Number: 5,736,556
[45] Date of Patent: Apr. 7, 1998

[54] TROPANE-2-ALDOXIME DERIVATIVES AS NEVRO TRANSMITTER REUPTAKE INHIBITORS

[75] Inventors: Peter Moldt, Humlebaek; Frank Wätjen, Herlev; Jørgen Scheel-Krüger, Glostrup, all of Denmark

[73] Assignee: NeuroSearch A/S, Glostrup, Denmark

[21] Appl. No.: 722,010

[22] PCT Filed: Apr. 12, 1995

[86] PCT No.: PCT/EP95/01358

§ 371 Date: Oct. 11, 1996

§ 102(e) Date: Oct. 11, 1996

[87] PCT Pub. No.: WO95/28401

PCT Pub. Date: Oct. 26, 1995

[30] Foreign Application Priority Data

Apr. 19, 1994 [DK] Denmark .................................. 0447/94
Nov. 24, 1994 [DK] Denmark .................................. 1338/94

[51] Int. Cl.$^6$ ........................ A61K 31/44; C07D 451/02; C07D 451/10

[52] U.S. Cl. .......................... 514/304; 546/124; 546/125; 546/132

[58] Field of Search ........................... 514/304; 546/124, 546/125, 132

[56] References Cited

FOREIGN PATENT DOCUMENTS 0604354  6/1994  European Pat. Off. ............... 514/304
0604355  6/1994  European Pat. Off. ............... 514/304

OTHER PUBLICATIONS

Journal of Medicinal Chemistry, vol. 34, No. 3, Mar. 1991 Washington US, pp. 883–886, F. Ivy Carroll et al., "Synthesis and ligand binding of cocaine isomers at the cocaine receptor".

Journal of Medicinal Chemistry, vol. 36, No. 24, Nov. 26, 1993 Washington US, pp. 3975–3977, Daniele Simoni et al., "Methoxylation of cocaine . . . ".

*Primary Examiner*—Alan L. Rotman
*Attorney, Agent, or Firm*—The Firm of Gordon W. Hueschen

[57] ABSTRACT

The present invention discloses compounds of the formula,

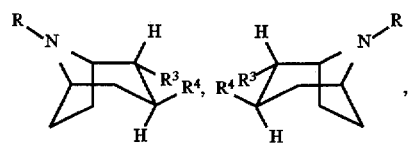

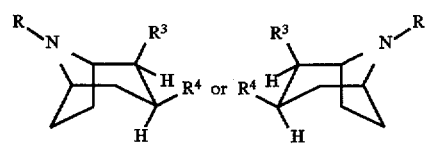

any mixture thereof, or a pharmaceutically acceptable salt thereof;

wherein R, $R^3$, and $R^4$ each have the meanings set forth in the specification.

The compounds possess valuable pharmaceutical properties as monoamine neurotransmitter, i.e dopamine, serotonin, noradrenalin, reuptake inhibitors.

22 Claims, 1 Drawing Sheet

TROPANE-2-ALDOXIME DERIVATIVES AS NEVRO TRANSMITTER REUPTAKE INHIBITORS

The present application is a U.S. national application filed under 35 USC 371 of PCT/EP95/01358, filed Apr. 12, 1995, which in turn is based upon the priority of Danish applications 0447/94, filed Apr. 19, 1994 and 1338/94, filed Nov. 24, 1994.

The present invention relates to novel oxime derivatives which are monoamine neurotransmitter, i.e dopamine, serotonin and noradrenalin, reuptake inhibitors. The present invention especially relates to novel oxime derivatives which are potent dopamine-reuptake inhibitors, and as such have pronounced anti-parkinsonian, antidepressant, anti-obesity, anti-narcolepsy and anti-drug-abuse activity and, at the same time, a low degree of undesired side effects; methods for the preparation of the novel oxime derivatives; pharmaceutical compositions containing the novel oxime derivatives; and methods for the treatment of parkinsonism, depression, obesity, narcolepsy and drug abuse, by administering a therapeutically effective amount of one or more of the novel oxime derivatives to a living animal body, including a human.

OBJECTS OF THE INVENTION

It is an object of the present invention to provide novel oxime derivatives having anti-parkinsonian, antidepressant, anti-obesity, anti-narcolepsy and anti drug abuse activity.

Another object of the invention is to provide novel pharmaceutical compositions containing the novel oxime derivatives which are useful for the treatment of parkinsonism, depression, obesity, narcolepsy and drug abuse.

Still another object of the invention is to provide a method of treating parkinsonism, depression, obesity, narcolepsy and drug abuse by administering a therapeutically effective amount of one or more of the novel oxime derivatives to a living animal body, including a human.

Other objects will become apparent hereinafter to one skilled in the art.

BRIEF DESCRIPTION OF THE DRAWINGS

Reference is now made to the drawings for a better understanding of the invention, wherein.

Figure 1:
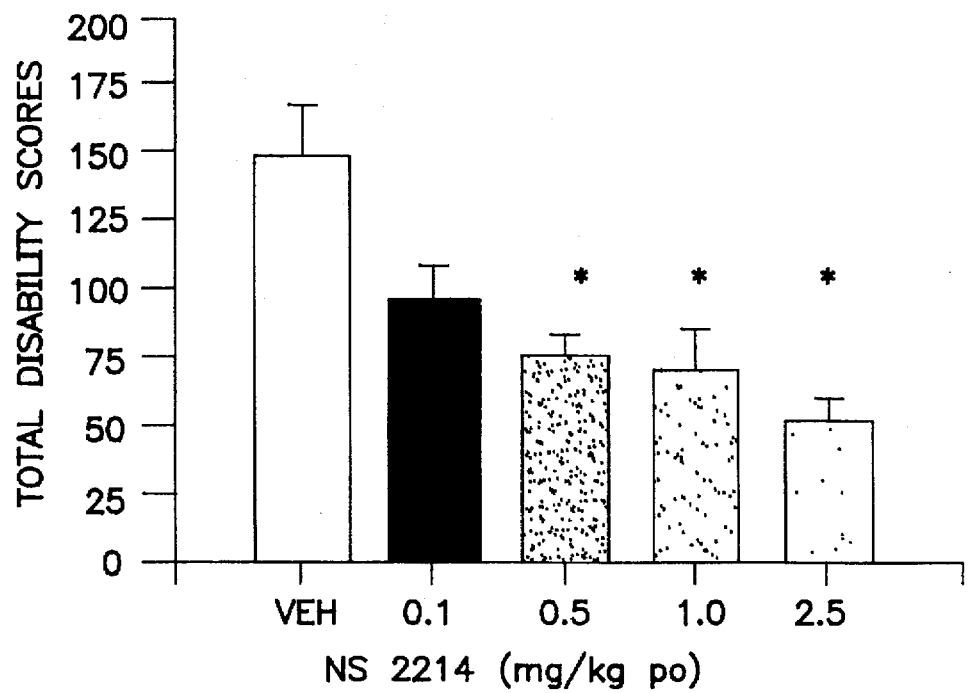
FIG. 1 is a graph showing that a compound of the invention identified as NS2214, at doses ranging from 0.1 to 2.5 mg/kg, causes a dose-dependent decrease in disability scores.

The column identified as "VEH", in each case identifies the results obtained when testing only the vehicle employed, the test being conducted as described in the Specification under the heading "Antagonism of MTPT-induced Parkinsonism in Marmoset Monkeys".

BACKGROUND OF THE INVENTION

Dopamine is released into the synaptic cleft in order to stimulate postsynaptic dopaminergic receptors. The removal of dopamine occurs normally by a reuptake mechanism into presynaptic terminals. By inhibiting this uptake an enhancement of the physiological dopaminergic activity occurs.

Compounds capable of inhibiting dopamine-reuptake are predicted to be useful in the treatment of Parkinson's disease, depression, cocaine addiction, obesity and narcolepsy.

A well known substance with both powerful dopamine releasing and dopamine-reuptake inhibiting properties, is cocaine. Cocaine has a variety of pharmacological actions, primarily a strong CNS stimulation and local anesthetic action. These effects are accompanied by high toxicity and dependence liability. (See for example R. L. Clarke et al in Journal of Medicinal Chemistry 16(11), 1261–1267 (1973)). The dependence liability is thought to be related to a combination of cocaine's powerful stimulant activity, short term of action, and rapid onset of action together with its strong dopamine releasing properties. It is believed, that compounds having long lasting selective dopamine reuptake-inhibiting properties, and being devoid of dopamine releasing properties, will be extremely useful as a novel type of anti-parkinsonian, antidepressant, anti-obesity and anti-narcolepsy agents. Furthermore such compounds will be extremely useful in the treatment of drug addiction, and especially in the treatment of cocaine addiction or misuse.

During the years many attempts have been made to optimize upon the properties of cocaine. Many derivatives of cocaine and of its isomers have been synthesized. See for example R. L. Clarke et al in Journal of Medicinal Chemistry 16(11), 1261–1267 (1973) and F. Ivy Caroll et al in Journal of Medicinal Chemistry 34, 883–886 (1991). Many of these derivatives and probably most pronounced the derivatives of R. L. Clarke et al above are very powerful stimulant compounds and have been found to be very potent dopamine reuptake inhibitors. However none of the cocaine derivatives synthesized until today have been found to be devoid of undesired side effects. Therefore, there is still a large need for novel dopamine-reuptake inhibitors.

Certain compounds provided herewith also possess potent serotonine (5-hydroxytryptamine, 5-HT) reuptake inhibiting activity in combination with their dopamine-reuptake inhibiting activity.

Pharmaceuticals currently used in antidepressant therapy, are inhibitors of noradrenalin-reuptake (Desipramine, Nortriptyline, and Protriptyline) or mixed serotonin-reuptake and noradrenaline-reuptake inhibitors (Imipramine and Amitriptyline). A serious drawback to these agents is their late onset of action (several weeks). It is predicted that a mixed serotonine-reuptake and dopamine-reuptake inhibitor may show a superior antidepressant effect with a rapid onset of action.

THE PRESENT INVENTION

The invention then, inter alia, comprises the following, alone or in combination:

The use of a compound having the formula,

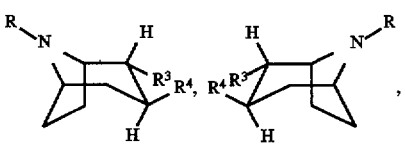

-continued

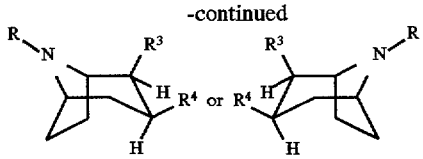

any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is CH=NOR', wherein R' is hydrogen or alkenyl, alkynyl, cycloalkyl, cycloalkylalkyl, aryl, or alkyl all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and
$R^4$ is
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;
benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl, for the manufacture of a medicament for the treatment of a disorder or disease of a living animal body, including a human, which disorder or disease is responsive to the inhibition of monoamine neurotransmitter reuptake in the central nervous system;
the use of a compound having the formula,

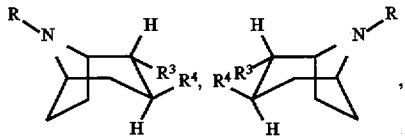

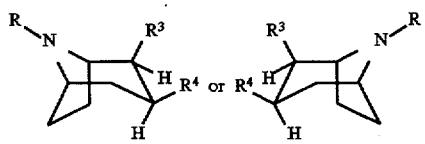

any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is CH=NOR', wherein R' is hydrogen or alkenyl, alkynyl, cycloalkyl, cycloalkylalkyl, aryl, or alkyl all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and
$R^4$ is
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;
benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl, for the manufacture of a medicament for the treatment of a disorder or disease of a living animal body, including a human, which disorder or disease is responsive to the inhibition of dopamine reuptake in the central nervous system;
the use of a compound having the formula,

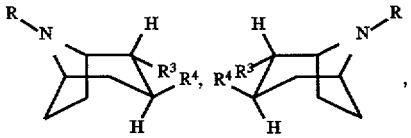

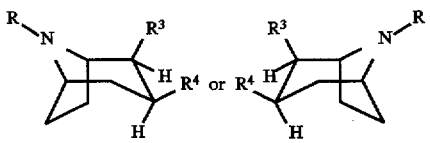

any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is CH=NOR', wherein R' is hydrogen or alkenyl, alkynyl, cycloalkyl, cycloalkylalkyl, aryl, or alkyl all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and
$R^4$ is
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;

benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;

heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl, for the manufacture of a medicament for the treatment of parkinsonism, depression, obesity, narcolepsy, or drug addiction and/or abuse;

the use as any above, wherein the compound employed is
3-(3,4-Dichlorophenyl)tropane-2-aldoxime,
3-(3,4-Dichlorophenyl)tropane-2-O-methyl-aldoxime
3-(3,4-Dichlorophenyl)tropane-2-O-benzyl-aldoxime,
3-(3,4-Dichlorophenyl)tropane-2-O-ethoxycarbonylmethyl-aldoxime,
3-(3,4-Dichlorophenyl)tropane-2-O-methoxycarbonylmethyl-aldoxime,
3-(3,4-Dichlorophenyl)tropane-2-O-(1-ethoxycarbonyl-1,1-dimethyl-methyl)-aldoxime,
3-(3,4-Dichlorophenyl)tropane-2-O-carboxymethyl-2-aldoxime,
N-Normethyl-3-(3,4-dichlorophenyl)tropane-2-O-methyl-aldoxime, or
N-Normethyl-3-(3,4-dichlorophenyl)tropane-2-O-benzyl-aldoxime,
or a pharmaceutically acceptable addition salt thereof;

the use as any above, wherein the compound employed is
(1R,2R,3S)-3-(3,4-Dichlorophenyl)tropane-2-aldoxime,
(1R,2R,3S)-3-(3,4-Dichlorophenyl)tropane-2-O-benzyl-aldoxime,
(1R,2R,3S)-3-(3,4-Dichlorophenyl)tropane-2-O-ethoxycarbonylmethyl-aldoxime,
(1R,2R,3S)-3-(3,4-Dichlorophenyl)tropane-2-O-methoxycarbonylmethyl-aldoxime,
(1R,2R,3S)-3-(3,4-Dichlorophenyl)tropane-2-O-(1-ethoxycarbonyl-1,1-dimethyl-methyl)-aldoxime,
(1R,2R,3S)-3-(3,4-Dichlorophenyl)tropane-2-O-carboxymethyl-2-aldoxime,
(1R,2R,3S)-N-Normethyl-3-(3,4-dichlorophenyl)tropane-2-O-methyl-aldoxime, or
(1R,2R,3S)-N-Normethyl-3-(3,4-dichlorophenyl)tropane-2-O-benzyl-aldoxime,
or a pharmaceutically acceptable addition salt thereof;

the use as any above, wherein the compound employed is
(1R,2R,3S)-3-(3,4-Dichlorophenyl)tropane-2-O-methyl-aldoxime, or a pharmaceutically acceptable addition salt thereof;

the use as above, wherein the compound employed is
the anti-isomere of (1R,2R,3S)-3-(3,4-Dichlorophenyl)tropane-2-O-methyl-aldoxime,
the syn-isomere of (1R,2R,3S)-3-(3,4-Dichlorophenyl)tropane-2-O-methyl-aldoxime,
a mixture thereof, or a pharmaceutically acceptable addition salt thereof;

a compound having the formula,

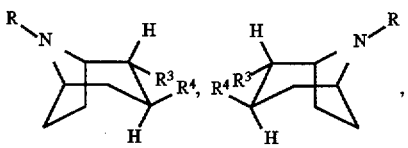

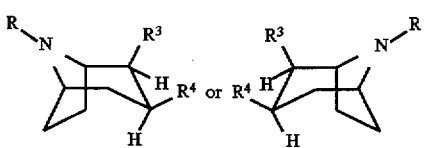

any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is CH=NOR', wherein R' is hydrogen or alkenyl, alkynyl, cycloalkyl, cycloalkylalkyl, aryl, or alkyl all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and
$R^4$ is
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;
benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
such a compound which is
3-(3,4-Dichlorophenyl)tropane-2-aldoxime,
3-(3,4-Dichlorophenyl)tropane-2-O-methyl-aldoxime
3-(3,4-Dichlorophenyl)tropane-2-O-benzyl-aldoxime,
3-(3,4-Dichlorophenyl)tropane-2-O-ethoxycarbonylmethyl-aldoxime,
3-(3,4-Dichlorophenyl)tropane-2-O-methoxycarbonylmethyl-aldoxime,
3-(3,4-Dichlorophenyl)tropane-2-O-(1-ethoxycarbonyl-1,1-dimethyl-methyl)-aldoxime,
3-(3,4-Dichlorophenyl)tropane-2-O-carboxymethyl-2-aldoxime,
N-Normethyl-3-(3,4-dichlorophenyl)tropane-2-O-methyl-aldoxime, or
N-Normethyl-3-(3,4-dichlorophenyl)tropane-2-O-benzyl-aldoxime,
or a pharmaceutically acceptable addition salt thereof;

such a compound which is
(1R,2R,3S)-3-(3,4-Dichlorophenyl)tropane-2-aldoxime,
(1R,2R,3S)-3-(3,4-Dichlorophenyl)tropane-2-O-benzyl-aldoxime,
(1R,2R,3S)-3-(3,4-Dichlorophenyl)tropane-2-O-ethoxycarbonylmethyl-aldoxime,
(1R,2R,3S)-3-(3,4-Dichlorophenyl)tropane-2-O-methoxycarbonylmethyl-aldoxime,
(1R,2R,3S)-3-(3,4-Dichlorophenyl)tropane-2-O-(1-ethoxycarbonyl-1,1-dimethyl-methyl)-aldoxime
(1R,2R,3S)-3-(3,4-Dichlorophenyl)tropane-2-O-carboxymethyl-2-aldoxime,
(1R,2R,3S)-N-Normethyl-3-(3,4-dichlorophenyl)tropane-2-O-methyl-aldoxime, or
(1R,2R,3S)-N-Normethyl-3-(3,4-dichlorophenyl)tropane-2-O-benzyl-aldoxime,
or a pharmaceutically acceptable addition salt thereof;

such a compound, which is (1R,2R,3S)-3-(3,4-Dichlorophenyl)-tropane-2-O-methyl-aldoxime, or a pharmaceutically acceptable addition salt thereof;

such a compound, which is
the anti-isomer of (1R,2R,3S)-3-(3,4-Dichlorophenyl) tropane-2-O-methyl-aldoxime,
the syn-isomer of (1R,2R,3S)-3-(3,4-Dichlorophenyl) tropane-2-O-methyl-aldoxime,
a mixture thereof, or a pharmaceutically acceptable addition salt thereof;

a method for the preparation of a compound as above comprising the step of reacting a compound having the formula

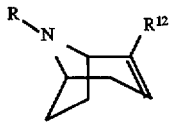

its enantiomere or mixtures thereof, wherein R is as defined above and $R^{12}$ is a carboxylic ester or $R^{12}$ have the meanings defined for $R^3$ above, with a compound having the formula $R^4$—A wherein $R^4$ is as defined above and A is any type of reactive functionality suitable for generating a carbanion as its counterpart, such as Li, MgX, wherein X is halogen, and CuLi, in a Michael like 1,4 addition reaction, and if $R^{12}$ is a carboxylic ester, conversion of the compound obtained to a compound of the invention, using conventional methods;

a pharmaceutical composition, comprising an effective amount of a compound as any above, or a pharmaceutically acceptable addition salt thereof, together with at least one pharmaceutically acceptable carrier or diluent;

a method of treating a disorder or disease of a living animal body, including a human, which disorder or disease is responsive to the inhibition of dopamine reuptake, comprising the step of administering to such a living animal body, including a human, in need thereof an effective amount of a compound having the formula,

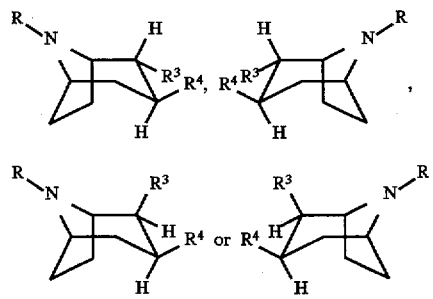

any mixture thereof, or a pharmaceutically acceptable salt thereof;
wherein
R is hydrogen, alkyl, alkenyl, alkynyl, cycloalkyl, cycloalkylalkyl or 2-hydroxyethyl;
$R^3$ is CH=NOR', wherein R' is hydrogen or alkenyl, alkynyl, cycloalkyl, cycloalkylalkyl, aryl, or alkyl all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and
$R^4$ is,
phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
3,4-methylenedioxyphenyl;
benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;
heteroaryl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; or
naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl; and
such a method, wherein parkinsonism, depression, obesity, narcolepsy, or drug addiction and/or abuse is treated.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, 1,2-, 2,3-, or 3,4-butenyl.

Alkynyl means a group of from two to six carbon atoms, including at least one triple bond, for example, but not limited to ethynyl, 2,3-propynyl, 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Cycloalkoxy is O-cycloalkyl, wherein cycloalkyl is as defined above.

Amino is $NH_2$ or NH-alkyl or N-(alkyl)$_2$, wherein alkyl is as defined above.

Heteroaryl is suitably a 5- or 6-membered heterocyclic monocyclic group. Such a heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl.

Aryl is an aromatic hydrocarbon, such as phenyl and naphthyl.

I.p. means intraperetoneally, which is a well known route of administration.

P.o. means peroral, which is a well known route of administration.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Furthermore, as the compounds of the invention are oximes they can exist in two forms, syn- and anti-form, depending on the arrangement of the substituents around the —C=N— double bond. The present invention includes both the syn- and anti-form of the compounds of the invention as well as mixtures thereof. Acids catalyzes anti-syn isomerization.

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

The following scheme illustrates one method by which the compounds of the invention can be prepared:

(i)

(1R,2S,3S) cis-form (1R,2R,3S) trans-form

In the above reaction-scheme, A is any type of reactive functionality suitable for generating a carbanion as its counterpart, such as Li, MgX, wherein X is halogen, and CuLi, in a Michael like 1,4 addition reaction, $R^{12}$ is a carboxylic ester, such as for example COO-Me, COO-Et, and COO-iPro, or $R^{12}$ is as defined for $R^3$ above, and R and $R^4$ is as defined above.

Both cis-form, trans-form and mixtures thereof can be obtained by the above reaction of a compound of formula (i) with $R^4$—A, but the compounds obtained are almost exclusively compounds wherein the substituent $R^4$ is in an equatorial position.

Isomerisation of the cis-isomer to form the trans-isomer can be affected in a strong base, such as an alcoholate.

The enantiomere of the cis- and trans-compounds in the scheme above can be obtained using the same procedure and the enantiomer of the compound of formula (i):

(iv)

as starting material.

Racemic mixtures of the cis- and trans-compounds respectively can be obtained using a mixture of compounds of formula (i) and (iv) as starting material.

Compounds obtained by the above method, wherein $R^{12}$ is a carboxylic ester can be converted to the compounds of the invention using conventional methods. Such methods includes reduction of the 2-carboxylic ester to 2-hydroxymethyl, followed by oxidation to the corresponding 2-aldehyde. The oximes of the invention can then be obtained by reaction of the 2-aldehyde compound with hydroxylamine-derivatives NH$_2$—OR', wherein R' is as defined above:

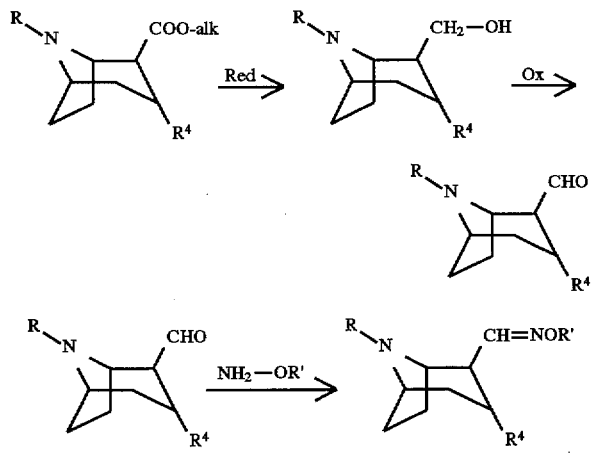

A compound of the invention can be converted to another compound of the invention using conventional methods.

Starting materials for the processses described in the present patent application are known or can be prepared by known processes from commercially available materials.

Starting materials of formula (i) wherein R$^{12}$ is a carboxylic acid ester can thus be obtained from cocaine using conventional methods, i.e. as described in the following examples.

Starting materials of formula (i) wherein R$^{12}$ is an oxime can be prepared using the same procedure as described above for the preparation of the oximes of the invention, and as described in EP-A2-316718.

The products of the reactions described herein are isolated by conventional means such as extraction, crystallization, distillation, chromatography, and the like.

BIOLOGY

The compounds of the present invention have been tested for their ability to bind to the dopamine transporter in the following tests for in vitro and in vivo inhibition of $^3$H-WIN 35428.

In vitro inhibition of $^3$H-WIN 35428 binding

Background

Dopamine transporters/uptake sites on nerve terminals presumably function to terminate neuronal signaling by removing dopamine from the synaptic cleft. The activity or presence of the dopamine transporter integral protein can be measured in vitro with synaptosomal uptake of $^3$H-dopamine or membrane binding assays with $^3$H-ligands known to bind to the transporter.

In vitro binding studies of cocaine have demonstrated that cocaine binds to the dopamine transporter and inhibits $^3$H-dopamine uptake. Numerous ligands of several structural types have been reported to bind at the dopamine uptake site, but it remains questionable whether their binding sites are identical to that of cocaine. A structural analog og cocaine, $^3$H-WIN 35428, binds selectively and with high affinity to the dopamine transporter complex.

Tissue preparation: Preparations are performed at 0°–4° C. unless otherwise indicated. Corpus striatum from male Wistar rats (150–200 g) is homogenized for 5–10 sec in 10 ml NaH$_2$PO$_4$ (50 mM, pH 7.4) using an Ultra-Turrax homogenizer. The suspension is centrifuged at 27,000×g for 15 min. The supernatant is discarded and the pellet is resuspended in 50 mM NaH$_2$PO$_4$, pH 7.4 (1000 ml per g of original tissue) and used for binding assays.

Assay: Aliquots of 0.5 ml tissue are added to 25 ml of test solution and 25 ml of $^3$H-WIN 35428 (1 nM, final concentration), mixed and incubated for 60 min at 2° C. Non-specific binding is determined using cocaine (30 mM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

25–75% inhibition of specific binding must be obtained, before calculation of an IC$_{50}$. The test value is given as IC$_{50}$ (the concentration (µM) of the test substance which inhibits the specific binding of $^3$H-WIN 35428 by 50%).

In vivo inhibition of $^3$H-WIN 35428 binding

Background $^3$H-WIN 35428 can also be used for in vivo receptor labelling studies in mice. Accumulation of $^3$H-WIN 35428 occurs preferentially in brain regions containing dopaminergic nerve terminals. The striatum which contains the highest concentration of dopamine has the highest accumulation of $^3$H-WIN 35428. The specific binding in the striatum reaches a maximum 30 min after an i.v. injection of $^3$H-WIN 35428 and this maximum is maintained for another 30 min. This specific binding of $^3$H-WIN 35428 can be partly or completely prevented by simultaneous or prior administration of drugs known to inhibit dopamine transport and ligand binding to the dopamine transporter complex, i.e., GBR 12909, cocaine and nomifensine (Scheffel et al., J. Pharm. Exp. Ther. 257, 954–958 (1991).

All test substances used are solutions or suspensions prepared in 10% TWEEN 80. Groups of three female NMRI mice (25 g) are injected i.p. with the test substance. Immediately after this injection the mice are injected i.v. via the tail vein with 2.0 mCi of $^3$H-WIN 35428 in 0.2 ml saline. Forty-five min after injection with all-WIN 35428, mice are killed by decapitation and striata dissected rapidly on ice. Tissues are weighed and dissolved for 36 h with 1 ml 2% sodium-laurylsulfat. The solubilized tissue is then added 2 ml of scintillation cocktail, and the amount of radioactivity per mg of tissue is counted by conventional liquid scintillation counting. Groups of untreated mice serves as controls. To determine non-specific binding groups of mice are injected with WIN 35428 (2.5 mg/kg) i.p. at the time of $^3$H-WIN 35428 injection. Specific binding is the amount of binding in controls minus the amount of binding in WIN 35428 treated mice.

The ED$_{50}$ value is determined from dose response curves. If only one dose of test substance is administered, the ED$_{50}$ value is calculated as follows, provided that the inhibition of specific binding is within the range of 25–75%:

ED$_{50}$=(administered dose, mg/kg)×1/(C$_o$/C$_x$−1), where C$_o$ is specific binding in controls and C$_x$ is the specific binding in mice treated with test substance.

The results obtained by testing compounds of the invention are given in the following table 1:

TABLE 1

| Test Compound | In vivo ED$_{50}$(mg/kg) | in vitro IC$_{50}$ μM |
|---|---|---|
| (1R,2R,3S)-3-(3,4-dichlorophenyl)-tropane-2-O-methyl-aldoxime, H$_2$SO$_4$ | 0.90 | 0.0030 |
| (1R,2R,3S)-3-(3,4-dichlorophenyl)tropane-2-aldoxime | 3.80 | 0.0034 |
| (1R,2R,3S)-3-(3,4-dichlorophenyl)-tropane-2-O-benzyl-aldoxime, HCl | >10.00 | 0.0760 |
| (1R,2R,3S)-3-(3,4-dichlorophenyl)-tropane-2-O-ethoxycarbonylmethyl-aldoxime, HCl | >10.00 | 0.024 |
| (1R,2S,3S)-3-(3,4-dichlorophenyl)-tropane-2-aldoxime | 0.56 | 0.0020 |
| (1R,2R,3S)-N-Normethyl-3-(3,4-dichlorophenyl)tropane-2-O-methyl-aldoxime, HCl | 1.4 | 0.006 |
| (1R,2R,3S)-3-(4-chlorophenyl)tropane-2-aldoxime | 1.05 | 0.013 |
| (1R,2R,3S)-3-(3,4-dichlorophenyl)tropane-2-O-(2-propynyl)-aldoxime, HCl | n.t. | 0.019 |
| (1R,2R,3S)-3-(3,4-dichlorophenyl)tropane-2-O-(2-propenyl)-aldoxime, HCl | n.t. | 0.022 |
| (1R,2R,3S)-3-(3,4-dichlorophenyl)-tropane-2-O-(2-methylpropyl)-aldoxime, HCl | n.t. | 0.056 |
| (1R,2R,3S)-3-(3,4-dichlorophenyl)-tropane-2-O-cyclopropylmethyl-aldoxime, HCl | n.t. | 0.02 |
| (1R,2R,3S)-3-(4-methylphenyl)tropane-2-O-methyl-aldoxime, HCl | n.t. | 0.042 |
| (1R,2S,3S)-3-(3,4-dichlorophenyl)-tropane-2-O-methyl-aldoxime | 0.37 | 0.0018 |
| (1R,2R,3S)-3-(4-chlorophenyl)tropane-2-O-methyl-aldoxime, HCl | 1.0 | 0.048 | n.t. = not tested

The test results presented above show that the compounds of the invention binds with high affinity to the dopamine transporter complex both in vitro and in vivo.

The compounds of the invention have also been tested for their ability to inhibit reuptake of dopamine(DA) noradrenalin(NA) and serotonin(5-HT) in synaptosomes.

Background

Specific neurotransmitter transporters/uptake sites on nerve terminals presumably function to terminate neuronal signaling by removing the neurotransmitters dopamine, noradrenaline and serotonin, respectively, from the synaptic cleft. The activity of the transporter integral proteins can be measured in vitro by synaptosomal uptake of $^3$H-dopamine, $^3$H-noradrenaline and $^3$H-serotonine, respectively.

In vitro inhibition of $^3$H-dopamine ($^3$H-DA) uptake in striatal synaptosomes Tissue preparations: Preparations are performed at 0°–4° C. unless otherwise indicated. Corpi striati from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supermatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Assay: Aliquots of 4.0 ml tissue suspension are added to 100 μl of test solution and 100 μl of $^3$H-DA (1 nM, final concentration), mixed and incubated for 25 min at 37° C. Non-specific uptake is determined using benztropine (10 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an IC$_{50}$.

The test value is given as IC$_{50}$ (the concentration (μM) of the test substance which inhibits the specific binding of $^3$H-DA by 50%).

In vitro inhibition of $^3$H-noradrenaline ($^3$H-NA) uptake in hippocampal synaptosomes Tissue preparation: Preparations are performed at 0°–4° C. unless otherwise indicated. Hippocampi from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (2000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 0.97 mM CaCl$_2$, 10 mM glucose and 1 mM ascorbic acid.

Assay: Aliquots of 4.0 ml tissue suspension are added to 100 μl of test solution and 100 μl of $^3$H-NA (1 nM, final concentration), mixed and incubated for 90 min at 37° C. Non-specific uptake is determined using desipramine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an IC$_{50}$.

The test value is given as IC$_{50}$ (the concentration (NM) of the test substance which inhibits the specific binding of $^3$H-NA by 50%).

In vitro inhibition of $^3$H-5-hydroxytryptamine $^3$H-5-HT, serotonin) uptake in cortical synaptosomes Tissue preparation: Preparations are performed at 0°–4° C. unless otherwise indicated. Cerebral cortices from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Assay: Aliquots of 4.0 ml tissue suspension are added to 100 μl of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-5-HT by 50%).

Test results obtained by testing selected compounds of the present invention will appear from the below table:

TABLE 2

| Test compound | DA-uptake $IC_{50}$(μM) | NA-uptake $IC_{50}$(μM) | 5-HT-uptake $IC_{50}$(μM) |
|---|---|---|---|
| (1R,2R,3S)-3-(3,4-dichlorophenyl)-tropane-2-O-methyl-aldoxime, $H_2SO_4$ | 0.003 | 0.0013 | 0.013 |
| (1R,2R,3S)-N-Normethyl-3-(3,4-dichlorophenyl)tropane-2-O-methyl-aldoxime, HCl | 0.002 | 0.0013 | 0.0017 |
| (1R,2R,3S)-3-(3,4-dichlorophenyl)-tropane 2-O-methyl-aldoxime, syn-isomere | 0.0034 | 0.0015 | n.t. | n.t. = not tested

The results presented above show that the compounds tested efficiently inhibits reuptake of dopamine, noradrenalin and serotonin in synaptosomes.

The compounds of the invention have also been tested in the following animal model for Parkinson's disease.

Antagonism of MTPT-induced Parkinsonism in Marmoset Monkeys

Background

Administration of MPTP (1-methyl-4-phenyl-1,2,3,6-tetrahydropyridine, hydrochloride) to monkeys induce a lesion of the dopaminergic system in the brain and gives rise to parkinsonian symptoms. By subsequent administration of test-compounds, the ability of the compounds to alleviate the parkinsonian signs can be tested.

Method

Common marmosets (weighing 350–400 g, aged 3–5 years and of either sex) were used in the study. Animals were housed alone under standard conditions at a temperature of 5°–27° C. and 50% relative humidity using a 12 hour light-dark cycle. Animals had free access to food and Water.

Some months before locomotor or behavioural testing began, animals were treated with MPTP (1-methyl-4-phenyl-1,2,3,6-tetrahydropyridine, hydrochloride) dissolved in sterile 0.9% saline in doses of 2 mg/kg administered subcutaneously daily for 5 days or until a clear parkinsonian state developed. The cumulative doses administered ranged between 8–12 mg/kg. During MPTP treatment and throughout the following 2–3 weeks the animals were hand fed until they had recovered enough to be able to feed themselves. Before behavioural testing, all animals showed a marked reduction in basal locomotor activity, poor coordination, reduced checking movements of the head, and abnormal posture of the spine and limbs in particular.

Test compounds was dissolved in 100% Tween 80 with warming to 40°–50° C. and then diluted with water. Test compounds was given by oral gavage in a volume of 2 ml/kg. In addition test compound vehicle was administered on each experimental day for comparison with drug treatments. Each animal was treated with vehicle or one of the three doses of test compound over the following weeks, with a one week period of recovery between treatments.

Rating of disability: The disability of animals were scored as follows; alertness (normal 0, sleepy 2); reaction to stimuli (normal 0, reduced 1, slow 2, absent 3); checking movements (present 0, reduced 1, absent 2); attention and eye movements (normal 0, abnormal 1); posture (normal 0, abnormal trunk 1, abnormal limbs 1, abnormal tail 1, or grossly abnormal 4); balance/coordination (normal 0, impaired 1, unstable 2, spontaneous falls 3); vocalization (normal 0, reduced 1, absent 2).

Measurement of locomotor activity: Locomotor activity was measured simultaneously for four individual animals each in a metal cage (50 w×60 l×70 h cm) with transparent plastic doors (50 w×70 h cm) similar to the home cages but fitted with eight horizontally orientated infrared photocells. These beams were located at floor level; across the cage, and one along each of two perches. Other beams were directed from front to back of the cage, at floor level and above each perch. Locomotor counts were measured as the number of light beam interuptions which occured as the animals moved about. These movement counts were accumulated in 30 minutes intervals and recorded for the 10 h duration of experimentation.

Data analysis: The mean (±) s.e.m. was calculated for time courses and accumulated locomotor counts or behavioural disability scores for the different treatment groups.

Figure 2:
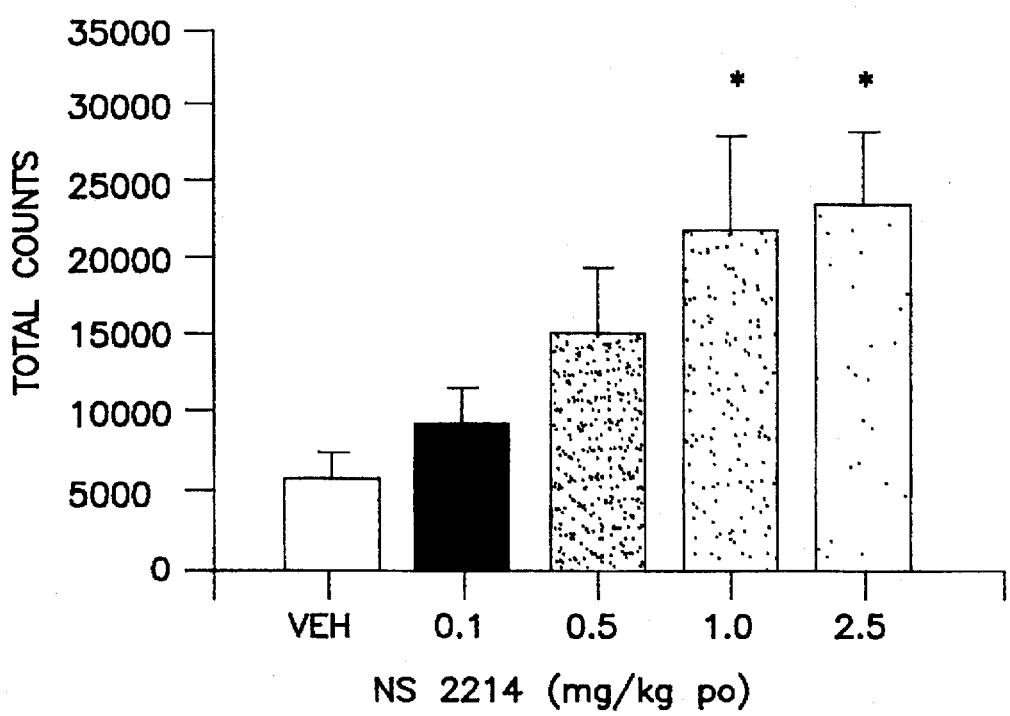
FIG. 2 is a graph showing that a compound of the invention identified as NS2214, at doses ranging from 0.1 to 2.5 mg/kg, causes a dose dependent increase in locomotor activity.

The results obtained by testing a compound of the invention (1R,2R,3S)-3-(3,4-dichlorophenyl)tropane-2O-methyl-aldoxime (NS 2214), are presented in FIGS. 1 and 2. From the Figure it is readily seen that the compound of the invention, at doses ranging from 0.1 to 2.5 mg/kg, causes a dose-dependent increase in locomotor activity and a dose dependent decrease in disability scores.

The compounds of the invention have also been tested in the following test for antidepressant activity.

Tail Suspension

Background

A decrease in the immobility time by mice suspended in their tail is seen after systemic administration of central stimulants and by antidepressants (Steru, L., Chermat, R., Thierry, B. & Simon, P. (1985) The tail suspension test: A new method for screening antidepressants in mice. Psychopharmacology 85:367–370.).

Method

Female NMRI mice (20–25 g) habituated to the room (12 hours light/dark) for at least 16 hours and housed 25 per cage are used. The mice are suspended by the tail with adhesive tape to a rod 30 cm above the lab. bench 30 min after an oral administation of vehicle or drug. For the next 6 min the accumulated duration of immobility defined as no movements by the body or extremities (however head movements are not defined as movements) are noted, Six mice per dose are used.

Saline or vehicle treated mice have immobility time scores between 160–180 sec in average. An $ED_{50}$-value is calculated by graphical interpolation from at least 3 doses as the dose reducing the immobility to 100 sec.

In the following table 4 results obtained by testing several compounds of the invention are presented:

TABLE 4

| Test compound | ED$_{50}$(mg/kg) |
|---|---|
| (1R,2R,3S)-3-(3,4-dichlorophenyl)tropane-2-aldoxime | 0.41 |
| (1R,2R,3S)-3-(3,4-dichlorophenyl)-tropane-2-O-methyl-aldoxime, H$_2$SO$_4$ | 0.1 |
| (1R,2R,3S)-3-(3,4-dichlorophenyl)-tropane-2-O-benzyl-aldoxime, HCl | 2 |
| (1R,2R,3S)-3-(3,4-dichlorophenyl)tropane-2-O-methoxycarbonylmethyl-aldoxime | 0.25 |
| (1R,2S,3S)-3-(3,4-dichlorophenyl)-tropane-2-aldoxime | 0.27 |
| (1R,2R,3S)-3-(3,4-dichlorophenyl)-tropane-2-O-(2-propenyl)-aldoxime | 0.23 |
| (1R,2R,3S)-N-Normethyl-3-(3,4-dichlorophenyl)tropane-2-O-methyl-aldoxime, HCl | 0.95 |
| (1R,2S,3S)-3-(3,4-dichlorophenyl)tropane-2-O-methyl-aldoxime | 0.4 |
| (1R,2S,3S)-3-(3,4-dichlorophenyl)-tropane-2-O-benzyl-aldoxime, HCl | 0.94 |
| (1R,2R,3S)-3-(4-chlorophenyl)tropane-2-aldoxime | 0.19 |
| (1R,2R,3S)-3-(3,4-dichlorophenyl)-tropane-2-O-(2-propynyl)-aldoxime | 0.04 |
| (1R,2R,3S)-3-(3,4-dichlorophenyl)-tropane-2-O-cyclopropylmethyl-aldoxime | 0.7 |
| (1R,2R,3S)-3-(3,4-dichlorophenyl)-tropane-2-O-(2-methylpropyl)-aldoxime | 0.8 |
| (1R,2R,3S)-3-(4-chlorophenyl)tropane-2-O-methyl-aldoxime, HCl | 0.43 |

The results presented in the table above, predict a potent antidepressive activity of the compounds of the invention.

Side Effect Profile of the Compounds of the Present Invention

The side effects of cocaine and the central stimulant amphetamine derivatives involve central excitement and stimulation in animals including primates and these effects can also be observed in humans. A serious side effect of cocaine and of the amphetamine derivatives includes also the ability to provoke toxic psychotic symptoms closely resembling the mental disease schizophrenia and these include halucinations, paranoia and abnormal bizarre stereotyped mental activity and stereotypy.

The current knowledge strongly indicates and suggests that these syndromes in primates and in humans are due to an extensive and massive release of dopamine within the striatal complex and in particular within the mesolimbic dopamine system, which innervates limbic structures including the nucleus accumbens.

The induction of stereotyped abnormal behavior in rodents thus also represents one of the most used animal models of schizophrenia in models for antipsychotic neuroleptic drugs (including haloperidol and chlorpromazine).

The development of toxic abnormal stereotyped amphetamine syndrome as described below may predict a toxic central stimulant side effect of dopamine releasing compounds in humans.

Classification of the Abnormal Stereotyped Behaviour

In general, the abnormal stereotyped behaviour after administration of amphetamine and cocaine-like central stimulant drugs can be classified into "low" and "high" intensity scores of stereotyped behaviour. The low intensity score of stereotypy includes an abnormal and continuous repetition of the locomotor, rearing and sniffing behaviour, and these syndromes are usually seen only after the lower doses of the central dopaminergic central stimulant drugs or may be seen present during the pre- and afterphases of the high doses. The low intensity behavioural effects are here included into the locomotor and rearing syndrome.

The high intensity syndrome of stereotypy is here considered, if the behavioural repertoire of the rat becomes strongly restricted in variation and consists of the continuous repetition of one or a few items of behaviour.

The syndrome of stereotyped sniffing behaviour is thus performed continuously on only a small restricted area of the cage. This activity usually starts on the upper part of the wall and following higher doses of the drugs increases in intensity to the performance of sniffing towards the lower part of the cage on the wall or on the wires of the floor. During this stage of high intensity stereotypy all normal behavioural elements are absent including behaviour such as eating, drinking, grooming and normal explorative investigation of the environment.

In rats, the high intensity sniffing can develop into sniffing associated with licking and/or biting-gnawing activity on the wire netting of the cage following still higher doses of the stimulant drugs. The rats are here usually sitting in a typical crouched posture in a corner of the cage. Backward locomotion may occasionally be observed.

The following rating scale is used for the high intensity stereotypy on the condition that the behavioural syndromes are as described above:

+=only stereotyped sniffing
++=stereotyped sniffing and episodic licking
+++=continuous licking and/or biting gnawing

TABLE

| Compound | Dose(p.o.) | Activity |
|---|---|---|
| (1R,2R,3S)-3-(3,4-Dichlorophenyl)-tropane-O-methyl-aldoxime | 15 mg/kg | +++ |

The dose of 15 mg/kg is the lowest dosis giving the activity indicated.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of parkinsonism, depression, obesity, narcolepsy, and drug abuse due to their potent dopamine uptake-inhibiting activity together with their low degree of undesired side-effects. These properties make the compounds of this invention extremely useful in the treatment of, parkinsonism, depression, obesity, narcolepsy, and drug abuse as well as other disorders sensitive to the dopamine uptake-inhibiting activity of the compounds of the present invention. The compounds of this invention may accordingly be administered to a living animal body, including a human, in need of treatment, alleviation, or elimination of an indication associated with or responsive to dopamine uptake-inhibiting activity. This includes especially parkinsonism, depression, obesity, narcolepsy, and drug abuse. Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

(−)-Anhydroecgonine methyl ester

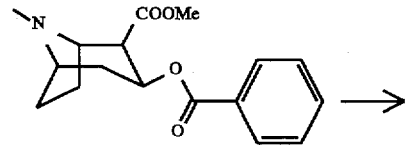

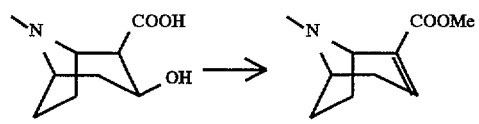

(1R,2R,3S)-2-Carbomethoxy-3-benzoxytropane, hydrochloride (100 g, 0.29 mol) was refluxed in 1000 ml 1M hydrochloric acid for 18 hours and the solution was ice cooled. Benzoic acid was collected by filtration and the filtrate was concentrated in vacuo. Trituration of the residue with ethanol and filtration yielded (1R,2R,3S)-3-hydroxytropane-2-carboxylate, hydrochloride as a white crystalline compound which without further purification was dried and refluxed in phosphorous oxychloride (50 ml) for two hours. The solution was concentrated in vacuo and absolute methanol (150 ml) was addition of a sodium hydroxide solution (10M, approximately 100 ml) and was extracted 5 times with diethyl ether. The combined organic phase was dried and concentrated in vacuo yielding oil, which was distilled in vacuo (70°–74° C., 1 mBar) yielding the title compound as clear oil.

EXAMPLE 2

(1R,2S,3S)-2-Carbomethoxy-3-(4-fluorophenyl) tropane and (1R,2R,3S)-2-carbomethoxy-3-(4-fluorophenyl)tropane

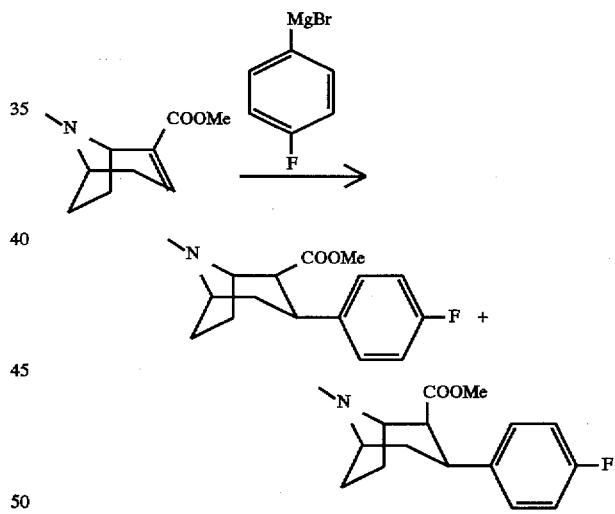

Grignard reagent was made in a three necked reaction flask equipped with mechanical stirring, an intensive condenser and a pressure equilibrated funnel, using 4-bromofluorobenzene (27.5 ml, 250 mmol) and magnesium turnings (6.3 g, 260 mmol) in 250 ml absolute diethyl ether. The solution of grignard reagent was cooled to −20° C. and a solution of (−)-anhydroecgonine methyl ester (21.7 g, 120 mmol) in 100 ml absolute diethyl ether was added over ½ hour. The reaction was stirred one hour at −20° C. and the reaction was quenched in one of the following two ways:

1) The reaction mixture was stirred into 250 ml crushed ice and the water phase was made acidic by addition of approximately 100 ml 4M hydrochloric acid. The organic phase was discharged and the water phase was washed with 100 ml diethyl ether. The water phase was made basic by addition of 25% ammonium hydroxide solution, and was then saturated with sodium chloride and was finally extracted three times with diethyl ether. The combined organic phase was dried and concentrated in vacuo yielding oil which was distilled in vacuo (150°–160° C., 2 mBar). This method yielded a mixture of two stereoisomers (2S/2R-1/3) which was separated by column chromatography using a mixture of diethyl ether and pentane (1+1)+1% triethyl amine as eluent. The crude products were triturated in pentane yielding (1R,2R,3S)-2-carbomethoxy-3-(4-fluorophenyl)tropane, white crystals m.p. 91°–92° C. and (1R,2R,3S)-2-carbomethoxy-3-(4-fluorophenyl)tropane, white crystals m.p. 65°–66° C.

2) The reaction mixture was cooled to −78° C. and a solution of trifluoroacetic acid (20 ml, 250 mmol) in 50 ml diethyl ether was added over 10 minutes. The cooling bath was removed and when the temperature had reached 0° C. the mixture was stirred into 700 ml water. The pH of the water phase was adjusted to pH 1 by addition of concentrated hydrochloric acid followed by aqueous work up and purification in the same way as described above. This method yielded a mixture of two stereoisomers (2S/2R-2/1).

The following compounds were made in a similar way:

(1R,2R,3S)-2-Carbomethoxy-3-benzyltropane and (1R,2S,3S)-2-carbomethoxy-3-benzyltropane, method 2, only (1R,2S,3S)-2-carbomethoxy-3-benzyltropane was obtained without contamination of the other isomer, as oil, which crystallize upon standing, m.p. 53°–54 C. (1R,2R,3S)-2-Carbomethoxy-3-benzyltropane was obtained by isomerisation of the mixture as described in example 3.

(1R,2R,3S)-2-Carbomethoxy-3-(4-chlorophenyl)tropane and (1R,2S,3S)-2-carbomethoxy-3-(4-chlorophenyl)tropane, method 2. The two isomers were not separated but the mixture was isomerized as described in example 3.

(1R,2R,3S)-2-Carbomethoxy-3-(4-chlorophenyl)tropane, (1R,2S,3S)-2-carbomethoxy-3-(4-chlorophenyl)tropane, (1S,2S,3R)-2-carbomethoxy-3-(4-chloro-phenyl)tropane and (1S,2R,3R)-2-carbomethoxy-3-(4-chlorophenyl)tropane, method 2. The two sets of enantiomeric pairs were not separated but the mixture was isomerized as described in example 3.

(1R,2R,3S)-2-Carbomethoxy-3-(4-methylphenyl)tropane and (1R,2S,3S)-2-carbomethoxy-3-(4-methylphenyl)tropane, method 2. The two isomers were not separated but the mixture was isomerized as described in example 3.

(1R,2S,3S)-2-Carbomethoxy-3-(2-naphthyl)tropane and (1R,2R,3S)-2-carbo-methoxy-3-naphthyl)tropane, method 2. Grignard reagent made by addition of a mixture of one equivalent 2-bromonaphthalene and 1,2-dibromoethane in diethyl ether to a refluxing suspension of two equivalents of magnesium. Both products were white crystalline compounds with m.p. 79°–80° C. and m.p. 86°–87° C. respectively.

(1R,2R,3S)-2-Carbomethoxy-3-(1-naphthyl)tropane and (1R,2S,3S)-2-carbo-methoxy-3-(1-naphthyl)tropane, hydrochloride, method 2. Grignard reagent made by addition of a mixture of one equivalent 1-bromonaphthalene and 1,2-dibromoethane in diethyl ether to a refluxing suspension of two equivalents of magnesium. The title compounds were isolated as respectively a white crystalline compound, m.p.133°–135° C. and an amorphous compound.

(1R,2S,3S)-2-Carbomethoxy-3-(3,4-dichlorophenyl)tropane and (1R,2R,3S)-2-carbomethoxy-3-(3,4-dichlorophenyl)tropane, method 2. Both products were white crystalline compounds with m.p. 69°–70° C. and 61°–63° C. respectively.

A racemic mixture of (1R,2R,3S)-2-Carbomethoxy-3-(3,4-dichlorophenyl)tropane and its enantiomere (1S,2S,3R)-2-Carbomethoxy-3-(3,4-dichlorophenyl)tropane, was prepared using (±)-anhydroecgonine methyl ester as starting material, method 2. Followed by isomerisation as described in example 3.

(1S,2S,3R)-2-carbomethoxy-3-(3,4-dichlorophenyl)tropane, was prepared using method 2. The compound was not isolated but isomerized as described in example 3.

(1R,2S,3S)-2-Carbomethoxy-3-(4-phenyl-phenyl)tropane and (1R,2R,3S)-2-carbomethoxy-3-(4-phenyl-phenyl)tropane, method 2. Both products were white crystalline compounds with m.p. 130°–132° C. and 95°–96° C. respectively.

(1R,2S,3S)-2-Carbomethoxy-3-(4-t-butyl-phenyl)tropane and (1R,2R,3S)-2-carbomethoxy-3-(4-t butyl-phenyl)tropane, method 2. Both products were white crystalline compounds with m.p. 84°–85° C. and 83°–84° C. respectively.

EXAMPLE 3

(1R,2R,3S)-2-Carbomethoxy-3-benzyltropane, hydrochloride

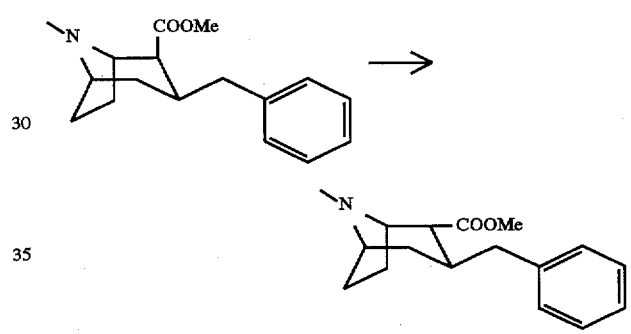

To a solution of (1R,2S,3S)-2-carbomethoxy-3-benzyltropane (5.6 g, 20.5 mmol) in absolute methanol (100 ml) was added a solution of sodium methanolate in methanol (2M, 2 ml) and the mixture was refluxed for 16 hours. The reaction mixture was concentrated in vacuo and the residue was dissolved in diethyl ether and was washed with water. The organic phase was dried and concentrated in vacuo. The crude product was purified by column chromatography using a mixture of diethyl ether and pentane (1+1)+1% triethyl amine as eluent yielding (1R,2R,3S)-2-carbomethoxy-3-benzyltropane as oil. By dissolution of this product in diethyl ether and subsequent addition of a solution of hydrochloric acid in diethyl ether the title compound precipitated as white crystals, m.p. 188°–190° C.

EXAMPLE 4

2-Carbomethoxy-3-tropanone

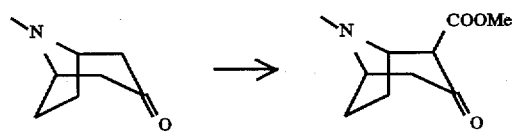

To a suspension of sodium hydride (3.2 g 80%, 107 mmol, prewashed in cyclohexane) and dimethylcarbonate (9.13 ml, 108 mmol) in absolute cyclohexane heated to reflux temperature, a solution of (±)-3-tropanone (6.9 g, 50 mmol) in 50 ml absolute cyclohexane was added over 15 minutes. No hydrogen evolution was apparent so 0.2 ml methanol was added. The reaction mixture was stirred over night at reflux temperature and after cooling to ambient temperature 75 ml water was carefully added. To the water phase was added 40 g ammonium chloride and the resulting mixture was extracted 8 times with methylene chloride. The combined methylene chloride organic phases were dried and concentrated in vacuo followed by column chromatography of the crude product using methylene chloride with increasing amounts (up to 10%) of methanol as eluent. The fractions containing the product were concentrated in vacuo and the resulting oil was subjected to kugelrohr destillation (1 mbar, 120° C., yielding the title compound as orange crystals, m.p. 104°–107° C.

EXAMPLE 5

2-Carbomethoxy-3-hydroxy-tropane, hydrochloride

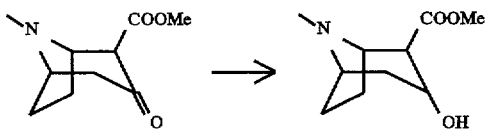

To a solution of the 2-carbomethoxy-3-tropanone obtained in example 4 (17 g, 85 mmol) in 750 ml methanol cooled to −35° C. was added sodium borohydride (17 g, 450 mmol) and the mixture was stirred for 4 hours. The cooled solution was quenched by slow addition of concentrated hydrochloric acid (40 ml) and the mixture was concentrated in vacuo. Water (400 ml) was added and the pH was adjusted to 3 by addition of concentrated hydrochloric acid. After having washed the water phase three times with diethyl ether pH was adjusted to 11 by addition of concentrated ammonium hydroxide and the water phase was extracted three times with methylene chloride. Concentration in vacuo yielded oil which was dissolved in ethanol and added concentrated hydrochloric acid followed by concentration in vacuo. Freeze drying of the residue yielded the title compound as an amorphous product.

(1S)-carbomethoxy-3-hydroxy-tropane, amorphous solid, was made in a similar way using as staffing material (1S)-2-carbomethoxy-3-tropanone obtained by resolution as described in *J. Med. Chem.*, 37, 2007(1994), of the compound obtained in example 4.

EXAMPLE 6

(1RS)-Anhydroecgonine methyl ester

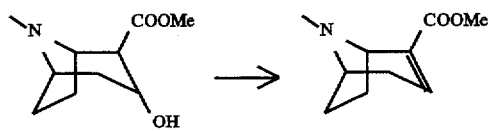

A mixture of 2-carbomethoxy-3-hydroxy-tropane, hydrochloride obtained in example 5 (0.5 g, 2.1 mmol) and thionyl chloride (0.4 ml, 5.3 mmol) was stirred at 60° C. for two hours resulting in a clear solution. After cooling to ambient temperature crushed ice was added and pH was adjusted to 11 by addition of concentrated ammonium hydroxide. The mixture was extracted twice with methylene chloride and the solvent was removed in vacuo yielding the title compound as oil which was destilled, 1 mbar 70–85° C.

(1S)-Anhydroecgonine methyl ester, oil, was made in a similar way using (1S)-carbomethoxy-3-hydroxy-tropane obtained in example 5 as starting material.

EXAMPLE 7

(1R,2R,3S)-N-Normethyl-2-carbomethoxy-3-(3,4-dichlorophenyl)tropane

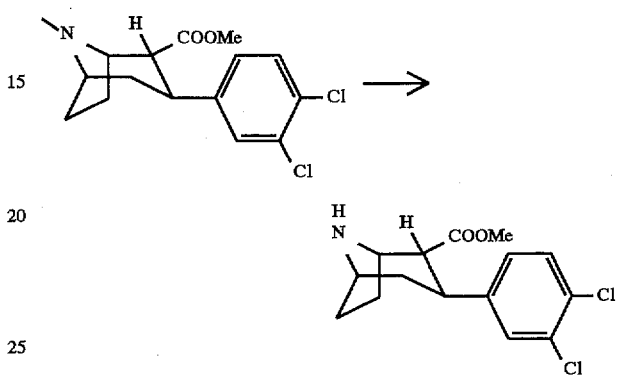

A mixture of (1R,2R,3S)-2-carbomethoxy-3-(3,4-dichlorophenyl)-tropane (8.7 g, 27 mmol) and 2,2,2-trichloroethyl chloroformate (14.6 ml, 106 mmol) in dry toluen (100 ml) was refluxed for 18 hours. The reaction mixture was concentrated in vacuo and to the residue was added methylene chloride which subsequently was washed with water. The organic phase was dried and concentrated in vacuo. The residue was dissolved in 75% aqueous acetic acid (60 ml) and zinc dust (8.7 g) was added to the reaction mixture which thereafter was stirred at ambient temperature for 18 hours. Concentrated ammonium hydroxide was added (pH>7), and the mixture was extracted twice with diethyl ether. The combined organic phase was dried and concentrated in vacuo yielding the title compound as oil which was used without further purification.

EXAMPLE 8

(1R,2R,3S)-N-Normethyl-N-(tert-butoxycarbonyl)-2-carbomethoxy-3-(3,4-dichlorophenyl)tropane

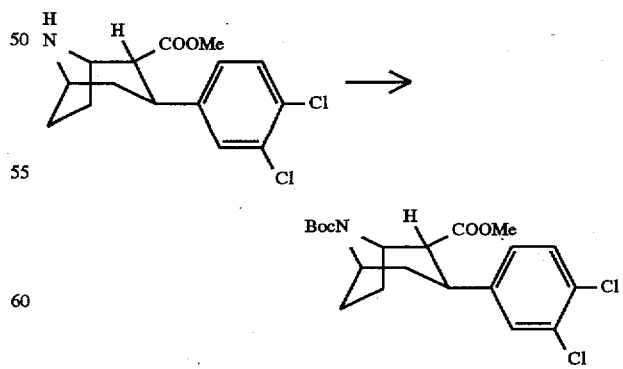

A solution of (1R,2R,3S)-N-normethyl-2-carbomethoxy-3-(3,4-dichlorophenyl)tropane (7 g, 22.3 mmol) and di-tert-butyl-dicarbonate (7.7 ml, 33.6 mmol) in dry tetrahydrofurane (50 ml) was stirred at room temperature for one hour. The reaction was quenched by addition of ice (100 ml) and the mixture was extracted twice with diethylether which was dried and concentrated in vacuo yielding the title compound as oil, which was used without further purification.

EXAMPLE 9

(1R,2S,3S)-2-Hydroxymethyl-3-(4-fluorophenyl)tropane

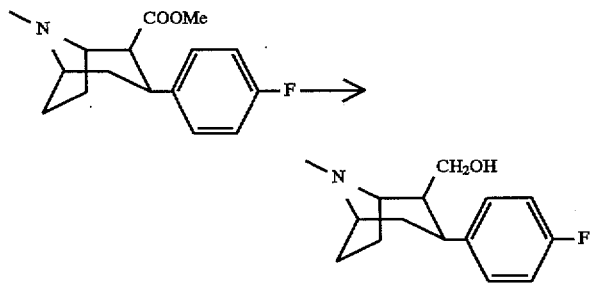

To a suspension of lithium aluminum hydride (0.8 g, 21 mmol) in diethyl ether (30 ml), at room temperature, was slowly added a solution of (1R,2S,3S)-2-carbomethoxy-3-(4-fluorophenyl)tropane (5 g, 18 mmol) in 100 ml diethyl ether. The reaction completed after stirring for 10 minutes and was quenched by addition of 0.8 ml water, 0.8 ml sodium hydroxide (15%) and 2 ml water. The aluminum salts were removed by filtration and the solvent was removed in vacuo leaving oil. The title compound precipitated upon trituration with pentane as white crystals, m.p. 79°–80° C.

The following compounds were made in a similar way:

(1R,2R,3S)-2-Hydroxymethyl-3-(4-fluorophenyl)tropane, white crystals, m.p. 169°–170° C.
(1R,2R,3S)-2-Hydroxymethyl-3-(3,4-dichlorophenyl)tropane, white crystals, m.p. 145°–150° C.
(1R,2R,3S)-N-Normethyl-N-(tert-butoxycarbonyl)-2-hydroxymethyl-3-(3,4-dichlorophenyl)tropane, oil.
(1R,2S,3S)-2-Hydroxymethyl-3-(3,4-dichlorophenyl)tropane, white crystals, m.p. 83°–89° C.
A racemic mixture of (1R,2R,3S)-2-Hydroxymethyl-3-(3,4-dichlorophenyl)tropane and its enantiomere (1S,2S,3R)-2-Hydroxymethyl-3-(3,4-dichlorophenyl)tropane, m.p. 186°–187° C.
(1S,2S,3R)-2-Hydroxymethyl-3-(3,4-dichlorophenyl)tropane, m.p. 179°–184° C.
(1R,2R,3S)-2-Hydroxymethyl-3-(4-chlorophenyl)tropane, white crystals, m.p. 200°–202° C.

EXAMPLE 10

(1R,2R,3S)-2-Formyl-3-(3,4-dichlorophenyl)tropane

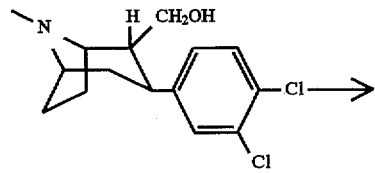

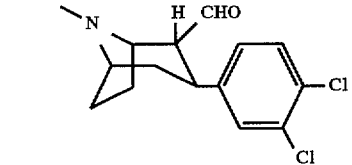

To a solution of oxalylchloride (2.3 ml) in absolute methylene chloride (60 ml) at –60° C., a solution of dimethylsulphoxide (4 ml) in absolute methylene chloride (10 ml) was added over 10 minutes. The mixture was stirred for 10 minutes and a suspension of (1R,2R,3S)-2-hydroxymethyl-3-(3,4-dichlorophenyl)tropane (7 g, 23.3 mmol) in absolute methylene chloride (400 ml) was added over 15 minutes. The resulting mixture was stirred for 10 minutes followed by addition of triethylamine (17 ml, 0.12 mmol) and stirring for another 10 minutes. The reaction mixture was allowed to reach ambient temperature and was quenched by addition of water (200 ml). The organic phase was washed twice with water, dried and concentrated in vacuo yielding the title compound as white crystals, m.p. 131°–135° C.

The following compounds were made in a similar way:
A racemic mixture of (1R,2R,3S)-2-Formyl-3-(3,4-dichlorophenyl)tropane and its enantiomere (1S,2S,3R)-2-Formyl-3-(3,4-dichlorophenyl)tropane, which was used without further purification.

(1S,2S,3R)-2-Formyl-3-(3,4-dichlorophenyl)tropane, which was used without further purification.
(1R,2R,3S)-2-Formyl-3-(4-chlorophenyl)tropane, which was used without further purification.
(1R,2R,3S)-N-Normethyl-N-(tert-butoxycarbonyl)-2-formyl-3-(3,4-dichlorophenyl)tropane, oil which was used without further purification.

The following compounds were made in a similar way, but the intermediate aldehyde was not isolated due to the risk of isomerization from the (1R,2S,3S) isomer to the (1R,2R,3S) isomer. Instead of warming the reaction mixture to ambient temperature and addition of water to quench the reaction mixture, an appropiate hydroxylammonium salt was added in excess (3 equivalents), and the mixture was allowed to reach ambient temperature at which it was stirred for 18 hours. The reaction mixture was washed twice with water and the organic phase was dried and concentrated in vacuo.

(1R,2S,3S)-3-(3,4-dichlorophenyl)tropane-2-aldoxime. Isolated by filtration of the reaction mixture as a mixture of syn/anti isomers 20%+80% (jugded by NMR) without identifying the identity of the two isomers. The product was not further purifyed, white crystals, m.p. 248°–251° C.

(1R,2S,3S)-3-(3,4-dichlorophenyl)tropane-2-O-methyl-aldoxime. Concentration of the methylene chloride phase left an oil, which was subjected to column chromatography using a mixture of methylene chloride, acetone and methanol (4+1+1) as eluent, yielding the title compound as white crystals, m.p. 98°–100° C.

(1R,2S,3S)-3-(3,4-dichlorophenyl)tropane-2-O-benzyl-aldoxime, hydrochloride. Concentration of the methylene chloride phase left an oil, which was subjected to column chromatography using ethyl acetate as eluent, yielding an oil. Finally the oil was dissolved in a small volume of diethyl ether and a solution of hydrochloric acid in diethyl ether was added yielding the title compound as white crystals, m.p. 196°–197° C.

EXAMPLE 11

(1R,2R,3S)-3-(3,4-Dichlorophenyl)tropane-2-aldoxime

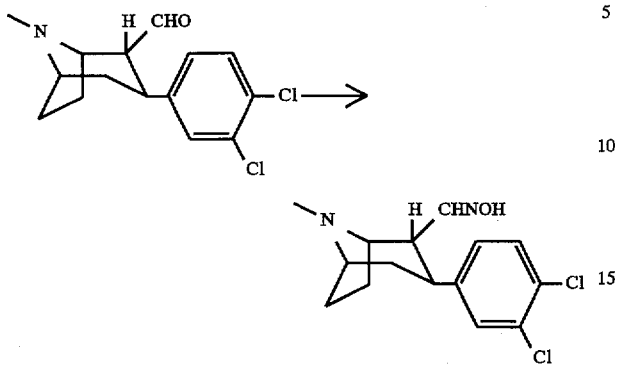

To a solution of (1R,2R,3S)-2-formyl-3-(3,4-dichlorophenyl)tropane (6.9 g, 23 mmol) in methanol (100 ml), sodium carbonate (4 g) and hydroxylammonium chloride (2.6 g, 37 mmol) were added, and the mixture was stirred at room temperature for 18 hours. The reaction mixture was concentrated in vacuo and the residue was triturated with water. A crude product was isolated by filtration and recrystallization first in a mixture of ethanol and water (1+1) and then in 99% ethanol yielded the title compound (mixture of syn/anti isomers—approximately 1+2) as white crystals, m.p. 230°–235° C.

The following compounds were made in a similar way:

(1R,2R,3S)-3-(4-chlorophenyl)tropane-2-O-aldoxime, white crystals, m.p. 220°–222° C.

(1R,2R,3S)-3-(4-chlorophenyl)tropane-2-O-methylaldoxime hydrochloride, white crystals, m.p. 90°–93° C.

(1R,2R,3S)-3-(3,4-Dichlorophenyl)tropane-2-O-methylaldoxime, oil.

A racemic mixture of (1R,2R,3S)-3-(3,4-dichlorophenyl)tropane-2-O-methyl-aldoxime and its enantiomere (1S,2S,3R)-3-(3,4-dichlorophenyl)tropane-2-O-methylaldoxime, m.p. 172°–178° C.

(1S,2S,3R)-3-(3,4-dichlorophenyl)tropane-2-O-methylaldoxime, m.p. 123°–130° C.

(1R,2R,3S)-3-(3,4-Dichlorophenyl)tropane-2-O-benzyl-aldoxime, white crystals, m.p. 161°–163° C.

(1R,2R,3S)-3-(3,4-Dichlorophenyl)tropane-2-O-phenyl-aldoxime, $H_2SO_4$, m.p. 100°–102° C.

(1R,2R,3S)-N-Normethyl-N-(tert-butoxycarbonyl)-3-(3,4-dichlorophenyl)tropane-2-O-methyl-aldoxime, oil which was used without further purification.

(1R,2R,3S)-N-Normethyl-N-(tert-butoxycarbonyl)-3-(3,4-dichlorophenyl)tropane-2-O-benzyl-aldoxime, oil which was used without further purification.

(1R,2R,3S)-3-(3,4-Dichlorophenyl)tropane-2-O-(2-propynyl)-aldoxime hydrochloride, white crystals, m.p.<100° C.

(1R,2R,3S)-3-(3,4-Dichlorophenyl)tropane-2-O-(2-propenyl)-aldoxime hydrochloride, white crystals, m.p. 131°–133° C.

(1R,2R,3S)-3-(3,4-Dichlorophenyl)tropane-2-O-(2-methylpropyl)-aldoxime hydrochloride, white crystals, m.p. 161°–163° C.

(1R,2R,3S)-3-(3,4-Dichlorophenyl)tropane-2-O-cyclopropylmethyl-aldoxime hydrochloride, white crystals, m.p. 173°–175° C.

(1R,2R,3S)-3-(3,4-Dichlorophenyl)tropane-2-O-ethyl-aldoxime hydrochloride, white crystals, m.p.<110° C.

(1R,2R,3S)-3-(3,4-Dichlorophenyl)tropane-2-O-(1,1-dimethylethyl)-aldoxime hydrochloride, white crystals, m.p. 213°–215° C.

(1R,2R,3S)-3-(4-methylphenyl)tropane-2-O-methyl-aldoxime hydrochloride, white crystals, m.p.<95° C. (hygroscopic)

Salts of (1R,2R,3S)-3-(3,4-dichlorophenyl)tropane-O-methyl-aldoxime was prepared as described below:

A solution of an acid (3.25 mmol) was added to a solution of (1R,2R,3S)-3-(3,4-dichlorophenyl)tropane-O-methyl-aldoxime (1 g, 3.0 mmol) in 96% ethanol (5 ml) and the mixture was stirred at room temperature. If no precipitate was observed after 18 hours, the mixture was concentrated in vacuo and the concentrated mixture was allowed to precipitate in the refrigerator. The crystalline product was isolated by filtration and washed with small amounts of ice cold 96% ethanol. The salt was recrystallised from either water or isopropanol.

The following salts of (1R,2R,3S)-3-(3,4-dichlorophenyl)tropane-2-O-methyl-aldoxime were obtained:

Maleate: white crystals, m.p. ($H_2O$) 140°–142° C.

Citrate: white crystals, m.p. (isopropanole) 143°–144° C.

Malonate: white crystals, m.p. (isopropanole) 116°–118° C.

Fumarate: white crystals, m.p. ($H_2O$) 158°–159° C.

$H_2SO_4$: white crystals, m.p. ($H_2O$) 84°–87° C. recrystallisation from $H_2O$ yields the disulphate salt, with some hydrogensulphate. Precipitation of the salt from isopropanole yields the hydrogensulphate, m.p. 161°–163° C.

HCl: white crystals, m.p. ($H_2O$) 74°–75° C.

EXAMPLE 12

(1R,2R,3S)-3-(3,4-Dichlorophenyl)tropane-2-O-ethoxycarbonylmethyl-aldoxime, hydrochloride

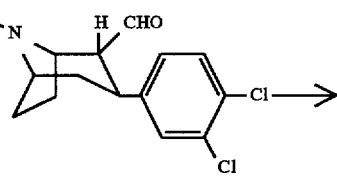

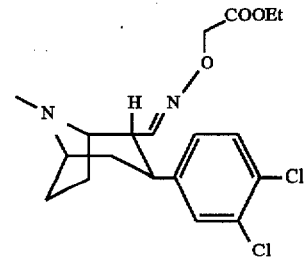

A solution of (1R,2R,3S)-2-formyl-3-(3,4-dichlorophenyl)tropane (1 g) O-(2-acetoxy)hydroxylammonium chloride (0.5 g) and concentrated hydrochloric acid in ethanol (1 ml) was refluxed for 5 hours followed by stirring for 18 hours at room temperature. The mixture was concentrated in vacuo and the residue was triturated with isopropanol. The title compound was isolated by filtration as white crystals, m.p. 220°–222° C.

The following compounds were made in a similar way:

(1R,2R,3S)-3-(3,4-Dichlorophenyl)tropane-2-O-methoxycarbonylmethyl-aldoxime, hydrochloride, white crystals, m.p. 193°–195° C.

(1R,2R,3S)-3-(3,4-Dichlorophenyl)tropane-2-O-(1-ethoxycarbonyl-1,1-dimethyl-methyl)-aldoxime, hydrochloride, white crystals, m.p. 214°–215° C.

(1R,2R,3S)-3-(4-chlorophenyl)tropane-2-O-methoxycarbonylmethyl-aldoxime hydrochloride, white crystals, m.p. 202°–203° C.

(1R,2R,3S)-3-(3,4-Dichlorophenyl)tropane-2-O-carboxymethyl-2-aldoxime), hydrochloride. Obtained together with (1R,2R,3S)-3-(3,4-dichloro-phenyl)tropane-2-O-methoxycarbonylmethyl-aldoxime, hydrochloride after reflux for one hour. White crystals, m.p. 158°–160° C.

EXAMPLE 13

(1R,2R,3S)-N-Normethyl-3-(3,4-dichlorophenyl)tropane-2-O-methyl-aldoxime, hydrochloride

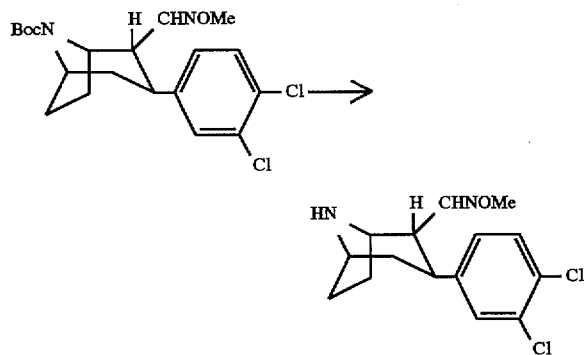

A mixture of (1R,2R,3S)-N-normethyl-N-(tert-butoxycarbonyl)-3-(3,4-dichloro-phenyl)tropane-O-methyl-aldoxime (1.3 g, 3.1 mmol) and trifluoroacetic acid (10 ml) in absolute methylene chloride (10 ml) was stirred for one hour. Ice and methylene chloride (50 ml) was added and pH of the mixture was adjusted to 10 by addition of 4M sodium hydroxide. The organic phase was dried and concentrated in vacuo yielding an oil, which was subjected to column chromatography using a mixture of methylene chloride, methanol and 25% ammonium hydroxide (90+10+1). The fractions containing the product were concentrated in vacuo, and the resulting oil was dissolved in a small amount of diethylether, and a solution of hydrochloric acid in diethylether was added. The title compound was isolated as white crystals, m.p. 226°–230° C.

The following compounds was made in a similar way:

(1R,2R,3S)-N-Normethyl-3-(3,4-dichlorophenyl)tropane-2-O-benzyl-aldoxime, hydrochloride, m.p. 70°–72° C.

(1R,2R,3S)-N-Normethyl-3-(4-chlorophenyl)tropane-2-aldoxime, malonate, m.p. 70°–75° C.

(1R,2R,3S)-N-Normethyl-3-(4-chlorophenyl)tropane-2-O-methyl-aldoxime, $H_2SO_4$.

EXAMPLE 14

Syn- and anti-isomers of (1R,2R,3S) and (1S,2S,3R)-3-(3,4-dichlorophenyl)tropane-O-methyl-aldoxime Formation of (1R,2R,3S) or (1S,2S,3R)-3-(3,4-dichlorophenyl)tropane-O-methyl-aldoxime by reaction of the corresponding 2-formyl compound and methoxyl ammonium chloride as described in example 12 yields a mixture of the syn- and anti-isomer, which is the result of a kinetic product control and isomerisation of the initially formed mixture. The kinetic mixture favours the anti-isomer (more than 90%) and the equilibrium mixture containing anti/syn in the ratio 7/3. The syn-anti equilibration is catalysed by acid and an equilibrium mixture can easily be obtained by heating an aqueous solution of the material at 100° C. and pH 4 for three hours. Column-chromatography of the equilibrium mixture using a mixture of toluene, ethyl acetate and triethylamine (2+1)+2% as eluent yields the syn-isomer as an oil, which can be kugelrohr destilled without isomerisation.

We claim:

1. A compound having the formula:

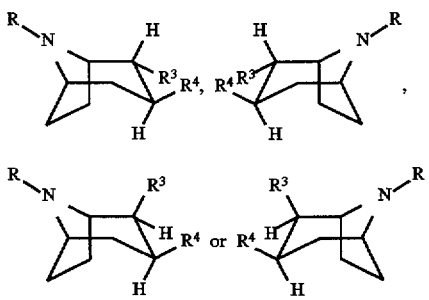

any mixture thereof, or a pharmaceutically acceptable salt thereof; wherein

R is hydrogen, alkyl, alkenyl, alkynyl, cycloalkyl, cycloalkylalkyl, or 2-hydroxyethyl;

$R^3$ is CH=NOR', wherein R' is hydrogen or alkenyl, alkynyl, cycloalkyl, cycloalkylalkyl, aryl, or alkyl, all of which may be substituted with COOH, COO-alkyl, COO-cycloalkyl, or phenyl which may be substituted one or more times with substituents selected from the group consisting of halogen, $CF_3$, CN, alkoxy, cycloalkoxy, alkyl, cycloalkyl, alkenyl, alkynyl, amino, and nitro; and $R^4$ is phenyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl and aryl;

3,4-methylenedioxyphenyl;

benzyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl, and aryl;

naphthyl which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl, and aryl.

2. A compound of claim 1 which is 3-(3,4-Dichlorophenyl)tropane-2-aldoxime, 3-(3,4-Dichlorophenyl)tropane-2-0-methyl-aldoxime 3-(3,4-Dichlorophenyl)tropane-2-0-benzyl-aldoxime, 3-(3,4-Dichlorophenyl)tropane-2-0-ethoxycarbonylmethyl-aldoxime, 3-(3,4-Dichlorophenyl)tropane-2-0-methoxycarbonylmethyl-aldoxime, 3-(3,4-Dichlorophenyl)tropane-2-0-(1-ethoxycarbonyl-1,1-dimethyl-methyl)-aldoxime,
3-(3,4-Dichlorophenyl)tropane-2-0-carboxymethylaldoxime,
N-Normethyl-3-(3,4-dichlorophenyl)tropane-2-0-methyl-aldoxime, or
N-Normethyl-3-(3,4-dichlorophenyl)tropane-2-0-benzyl-aldoxime,
or a pharmaceutically acceptable addition salt of any of the foregoing.

3. A compound of claim 1 which is
(1R,2R,3S)-3-(3,4-Dichlorophenyl)tropane-2-aldoxime,
(1R,2R,3S)-3-(3,4-Dichlorophenyl)tropane-2-0-benzyl-aldoxime,
(1R,2R,3S)-3-(3,4-Dichlorophenyl)tropane-2-0-ethoxycarbonylmethyl-aldoxime,
(1R,2R,3S)-3-(3,4-Dichlorophenyl)tropane-2-0-methoxycarbonylmethyl-aldoxime,
(1R,2R,3S)-3-(3,4-Dichlorophenyl)tropane-2-0-(1-ethoxycarbonyl-1,1-dimethyl-methyl)-aldoxime,
(1R,2R,3S)-3-(3,4-Dichlorophenyl)tropane-2-0-carboxymethyl-2-aldoxime,
(1R,2R,3S)-N-Normethyl-3-(3,4-dichlorophenyl)tropane-2-0-methyl-aldoxime, or
(1R,2R,3S)-N-Normethyl-3-(3,4-dichlorophenyl)tropane-2-0-benzyl-aldoxime,
or a pharmaceutically acceptable addition salt of any of the foregoing.

4. A compound of claim 1, which is (1R,2R,3S)-3-(3,4-Dichlorophenyl)-tropane-2-0-methyl-aldoxime, or a pharmaceutically acceptable addition salt thereof.

5. A compound of claim 4, which is
the anti-isomere of (1R,2R,3S)-3-(3,4-Dichlorophenyl)tropane-2-0-methyl-aldoxime,
the syn-isomere of (1R,2R,3S)-3-(3,4-Dichlorophenyl)tropane-2-0-methyl-aldoxime,
a mixture thereof, or a pharmaceutically acceptable addition salt of any of the foregoing.

6. A pharmaceutical composition, comprising an effective amount of a compound of claim 1, or a pharmaceutically acceptable addition salt thereof, together with at least one pharmaceutically acceptable carrier or diluent.

7. A method of treating a disorder or disease of a living animal body, including a human, which disorder or disease is responsive to the inhibition of dopamine reuptake comprising the step of administering to such a living animal body, including a human, in need thereof an effective amount of a compound of claim 1.

8. The method of claim 7 wherein parkinsonism, depression, obesity, narcolepsy or drug addiction and/or abuse is treated.

9. A pharmaceutical composition of claim 6, wherein the compound is
(3,4-Dichlorophenyl)tropane-2-aldoxime,
(3,4-Dichlorophenyl)tropane-2-O-methyl-aldoxime
(3,4-Dichlorophenyl)tropane-2-benzyl-aldoxime,
(3,4-Dichlorophenyl)tropane-2-O-ethoxycarbonylmethyl-aldoxime,
(3,4-Dichlorophenyl)tropane-2-O-methoxycarbonylmethyl-aldoxime,
(3,4-Dichlorophenyl)tropane-2-O-(1-ethoxycarbonyl-1,1-dimethyl-methyl)-aldoxime,
(3,4-Dichlorophenyl)tropane-2-O-carboxymethyl-2-aldoxime,
N-Normethyl-3-(3,4-dichlorophenyl)tropane-2-O-methyl-aldoxime, or
N-Normethyl-3-(3,4-dichlorophenyl)tropane-2-O-benzyl-aldoxime,
or a pharmaceutically acceptable addition salt thereof.

10. A pharmaceutical composition of claim 6, wherein the compound is
(1R,2R,3S)-3-(3,4-Dichlorophenyl)tropane-2-aldoxime,
(1R,2R,3S)-3-(3,4-Dichlorophenyl)tropane-2-O-benzyl-aldoxime,
(1R,2R,3S)-3-(3,4-Dichlorophenyl)tropane-2-O-ethoxycarbonylmethyl-aldoxime,
(1R,2R,3S)-3-(3,4-Dichlorophenyl)tropane-2-O-methoxycarbonylmethyl-aldoxime,
(1R,2R,3S)-3-(3,4-Dichlorophenyl)tropane-2-O-(1-ethoxycarbonyl-1,1dimethyl-methyl)-aldoxime,
(1R,2R,3S)-3-(3,4-Dichlorophenyl)tropane-2-O-carboxymethyl-2-aldoxime,
(1R,2R,3S)-N-Normethyl-3-(3,4-dichlorophenyl)tropane-2-O-methyl-aldoxime, or
(1R,2R,3S)-N-Normethyl-3-(3,4-dichlorophenyl)tropane-2-O-benzyl-aldoxime,
or a pharmaceutically acceptable addition sail thereof.

11. A pharmaceutical composition of claim 6, wherein the compound is
(1R,2R,3S)-3-(3,4-Dichlorophenyl)tropane-2-O-methyl-aldoxime, or a pharmaceutically acceptable addition salt thereof.

12. A pharmaceutical composition of claim 6, wherein the compound is
the anti-isomere of (1R,2R,3S)-3-(3,4-Dichlophenyl)tropane-2-O-methyl-aldoxime,
the syn-isomere of (1R,2R,3S)-3-(3,4-Dichlorophenyl)tropane-2-O-methyl-aldoxime,
a mixture thereof, or a pharmaceutically acceptable addition salt thereof.

13. A method of claim 7, wherein the compound is
3-(3,4-Dichlorophenyl)tropane-2-aldoxime,
3-(3,4-Dichlorophenyl)tropane-2-O-methyl-aldoxime
3-(3,4-Dichlorophenyl)tropane-2-O-benzyl-aldoxime,
3-(3,4-Dichlorophenyl)tropane-2-O-ethoxycarbonylmethyl-aldoxime,
3-(3,4-Dichlorophenyl)tropane-2-O-methoxycarbonylmethyl-aldoxime,
3-(3,4-Dichlorophenyl)tropane-2-O-(1-ethoxycarbonyl-1,1-dimethyl-methyl)-aldoxime,
3-(3,4-Dichlorophenyl)tropane-2-O-carboxymethyl-2-aldoxime,
N-Normethyl-3-(3,4-dichlorophenyl)tropane-2-O-methyl-aldoxime, or
N-Normethyl-3-(3,4-dichlorophenyl)tropane-2-O-benzyl-aldoxime,
or a pharmaceutically/acceptable addition salt thereof.

14. A method of claim 7 wherein the compound is
(1R,2R,3S)-3-(3,4-Dichlorophenyl)tropane-2-aldoxime,
(1R,2R,3S)-3-(3,4-Dichlorophenyl)tropane-2-O-benzyl-aldoxime,
(1R,2R,3S)-3-(3,4-Dichlorophenyl)tropane-2-O-ethoxycarbonylmethyl-aldoxime,
(1R,2R,3S)-3-(3,4-Dichlorophenyl)tropane-2-O-methoxycarbonylmethyl-aldoxime,
(1R,2R,3S)-3-(3,4-Dichlorophenyl)tropane-2-O-(1-ethoxycarbonyl-1,1-dimethyl-methyl)-aldoxime,
(1R,2R,3S)-3-(3,4-Dichlorophenyl)tropane-2-O-carboxymethyl-2-aldoxime,
(1R,2R,3S)-N-Normethyl-3-(3,4-dichlorophenyl)tropane-2-O-methyl-aldoxime, or
(1R,2R,3S)-N-Normethyl-3-(3,4-dichlorophenyl)tropane-2-O-benzyl-aldoxime,
or a pharmaceutically acceptable addition salt thereof.

15. A method of claim 7, wherein the compound is (1R,2R,3S)-1-(3,4-Dichlorophenyl)tropane-2-O-methyl-aldoxime, or a pharmaceutically acceptable addition salt thereof.

16. A method of claim 7, wherein the compound is
the anti-isomere of (1R,2R,3S)-3-(3,4-Dichlorophenyl) tropane-O-methyl-aldoxime,
the syn-isomere of (1R,2R,3S)-3-3,4-Dichlorophenyl) tropane-2-O-methyl-aldoxime,
a mixture thereof, or a pharmaceutical acceptable addition salt thereof.

17. The method of claim 8, wherein Parkinsonism is treated.

18. The method of claim 17, wherein the compound employed is
(1R,2R,3S)-3-(3,4-Dichlorophenyl)-tropane-2-O-methyl-aldoxime,
or a pharmaceutically-acceptable addition salt thereof.

19. The method of claim 8, wherein cocaine addiction or misuse is treated.

20. The method of claim 19, wherein the compound employed is
(1R,2R,3S)-3-(3,4-Dichlorophenyl)-tropane-2-O-methyl-aldoxime,
or a pharmaceutically-acceptable addition salt thereof.

21. A process for the preparation of a compound of claim 1 comprising the step of reacting a compound having the formula

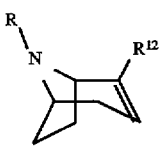

its enantiomers or mixtures thereof, wherein R is as defined in claim 1 and $R^{12}$ is a carboxylic ester or $R^{12}$ has the meanings defined for $R^3$ in claim 1, with a compound having the formula $$R^4—A$$

wherein $R^4$ is as defined in claim 1 and A is any type of reactive functionality suitable for generating a carbanion as its counterpart, in a Michael like 1,4 addition reaction and, if $R^{12}$ is a carboxylic ester, conversion of the compound obtained to a compound of claim 1, using conventional methods.

22. A method of claim 21, wherein A is selected from the group consisting of Li, MgX wherein X is halogen, and CuLi.

* * * * *

UNITED STATES PATENT AND TRADEMARK OFFICE
CERTIFICATE OF CORRECTION

PATENT NO. : 5,736,556
DATED : April 7, 1998
INVENTOR(S) : P. Moldt, F. Watjen, J. Scheel-Kruger Page 1 of 3

It is certified that error appears in the above-indentified patent and that said Letters Patent is hereby corrected as shown below:

Title Page, [54], "TROPANE-2-ALDOXIME DERIVATIVES AS NEVRO TRANSMITTER REUPTAKE INHIBITORS" should read -- TROPANE-2-ALDOXIME DERIVATIVES AS NEURO TRANSMITTER REUPTAKE INHIBITORS --.

Column 1, line 1 through 3: Title should read -- TROPANE-2-ALDOXIME DERIVATIVES AS NEURO TRANSMITTER REUPTAKE INHIBITORS --.

Column 2, line 47: "noradrenaline-" should read -- noradrenalin --.

Column 10, line 53: "enantiomere" should read -- enantiomer --.

Column 12, line 46: "all-WIN" should read -- $^3$H-WIN --.

Column 13, line 44: "noradrenaline" should read -- noradrenalin --.

UNITED STATES PATENT AND TRADEMARK OFFICE
CERTIFICATE OF CORRECTION

PATENT NO. : 5,736,556
DATED : April 7, 1998
INVENTOR(S) : P. Moldt, F. Watjen, J. Scheel-Kruger Page 2 of 3

It is certified that error appears in the above-indentified patent and that said Letters Patent is hereby corrected as shown below:

Column 16, line 37: "the Figure it" should read
-- the Figures it --.

Column 21, line 31: "invention am" should read
-- invention are --.

Column 22, line 1: Insert, between "was" and "addition" the following: -- slowly added under ice cooling. The solution was stirred at ambient temperature for 16 hours and was concentrated in vacuo. The residue was ice cooled and made basic by --.

Column 33, lines 53,54,55,56,58,60,& 62: At the beginning of each line, insert: -- 3- --.

Column 33, line 55: In the middle of the line, "-2-" should read -- -2-O- --.

Column 35, line 1: At the beginning of the line, "(1R,2R,3S)-1-" should read -- (1R,2R,3S)-3- --

Column 35, line 6: "tropane-O-" should read
-- tropane-2-O- --.

UNITED STATES PATENT AND TRADEMARK OFFICE
CERTIFICATE OF CORRECTION

PATENT NO. : 5,736,556
DATED : April 7, 1998
INVENTOR(S) : P. Moldt, F. Watjen, J. Scheel-Kruger It is certified that error appears in the above-indentified patent and that said Letters Patent is hereby corrected as shown below:

Column 35, line 7: "(1R,2R,3S)-3-3,4-" should read
 -- (1R,2R,3S)-3-(3,4- --.

Column 36, line 22: At the beginning of the line,
 "A method" should read -- A process --.

Signed and Sealed this

Seventh Day of July, 1998

Attest:

Attesting Officer

BRUCE LEHMAN
Commissioner of Patents and Trademarks